United States Patent [19]

Roane

[11] Patent Number: 5,035,620

[45] Date of Patent: Jul. 30, 1991

[54] ENDODONTIC POST WITH SPIRAL GROOVE

[76] Inventor: James B. Roane, 707 SW. 24th St., Ste. 201, Norman, Okla. 73069

[21] Appl. No.: 308,046

[22] Filed: Feb. 9, 1989

[51] Int. Cl.$^5$ .............................................. A61C 5/08
[52] U.S. Cl. .................................... 433/221; 433/224
[58] Field of Search ................. 433/220, 221, 224, 225

[56] References Cited

U.S. PATENT DOCUMENTS

| | | | |
|---|---|---|---|
| D. 273,984 | 5/1984 | Vlock | D24/10 |
| 430,522 | 6/1890 | Genese . | |
| 659,196 | 10/1900 | Johnson | 433/221 |
| 758,750 | 5/1904 | Haldeman . | |
| 1,119,407 | 12/1914 | Davis . | |
| 2,536,669 | 1/1951 | Thau-Jensen | 433/221 |
| 3,590,486 | 7/1971 | Brenner et al. | 32/15 |
| 3,675,328 | 7/1972 | Weissman | 32/15 |
| 3,675,329 | 7/1972 | Weissman | 32/15 |
| 3,728,794 | 4/1973 | Edelman | 32/15 |
| 3,740,851 | 6/1973 | Weissman | 32/15 |
| 3,861,043 | 1/1975 | Lieb et al. | 32/15 |
| 3,874,081 | 4/1975 | Franklin et al. | 32/15 |
| 4,060,896 | 12/1977 | Wahnish | 32/10 A |
| 4,175,565 | 11/1979 | Chiarenza et al. | 433/174 X |
| 4,229,169 | 10/1980 | Smith et al. | 433/174 |
| 4,234,309 | 11/1980 | Sellers | 433/225 |
| 4,259,076 | 3/1981 | Yanney | 433/225 |
| 4,268,253 | 5/1981 | Gross et al. | 433/221 |
| 4,276,027 | 6/1981 | Lustig | 433/225 |
| 4,290,756 | 9/1981 | Sellers | 433/225 |
| 4,348,183 | 9/1982 | Weissman | 433/221 |
| 4,349,335 | 9/1982 | Weissman | 433/225 |
| 4,365,958 | 12/1982 | Vlock | 433/225 |
| 4,397,634 | 8/1983 | Biggs | 433/225 |
| 4,431,416 | 2/1984 | Niznick | 433/174 |
| 4,468,200 | 8/1984 | Munch | 433/174 |
| 4,479,783 | 10/1984 | Weissman | 433/221 |
| 4,490,116 | 12/1984 | Deutsch et al. | 433/215 |
| 4,500,296 | 2/1985 | Friedman | 433/225 |
| 4,579,532 | 4/1986 | Lustig | 433/225 |
| 4,600,392 | 7/1986 | Weissman | 433/225 |
| 4,655,711 | 4/1987 | Weissman | 433/225 |
| 4,708,655 | 11/1987 | Weissman | 433/225 |
| 4,713,004 | 12/1987 | Linkow et al. | 433/174 |
| 4,713,006 | 12/1987 | Hakamatsuka et al. | 433/201.1 |
| 4,729,736 | 3/1988 | Weissman | 433/221 |
| 4,758,160 | 7/1988 | Ismail | 433/173 |
| 4,762,492 | 8/1988 | Nagai | 433/174 |
| 4,767,332 | 8/1988 | Weissman | 433/225 |

OTHER PUBLICATIONS

CDA Journal, "Preparing Severely Damaged Teeth", by Shillingburg, Jr., et al., Mar., 1983, pp. 85-91.
Exhibit A—photograph of Model C-1 post made by the Parkall Company.
Exhibit B—photograph of a post manufactured by Dentatus.
Exhibit C—photograph of BCH post.
Exhibit D—photograph of a post made by Parapost.
Exhibit E—photograph of another post manufactured by Parapost.
Exhibit F—photograph of several posts manufactured by Kurer.
Exhibit G—photograph of a post constructed generally like that shown in U.S. Pat. No. 4,479,783 to Weissman at FIGS. 2 and 3.
Exhibit H—photograph of a post having an external spiral thread along with a vertical vent groove.

*Primary Examiner*—Robert P. Swiatek
*Assistant Examiner*—Nicholas D. Lucchesi
*Attorney, Agent, or Firm*—Laney, Dougherty, Hessin & Beavers

[57] ABSTRACT

An endodontic post has an elongated cylindrical outer surface. One and only one groove having a pitch angle in a range of from about 35° to about 55° is disposed in the cylindrical outer surface. The groove performs three functions. It vents air and/or cement as the post is placed in a prepared post space. It aids in retaining the post in place within the post space after the cement is set. It also acts as a thread so that the post can be unthreaded and removed from the post space if necessary. The dimensions of the groove are such that an ungrooved area of the outer cylindrical surface is substantially greater than a grooved area thereof.

10 Claims, 1 Drawing Sheet

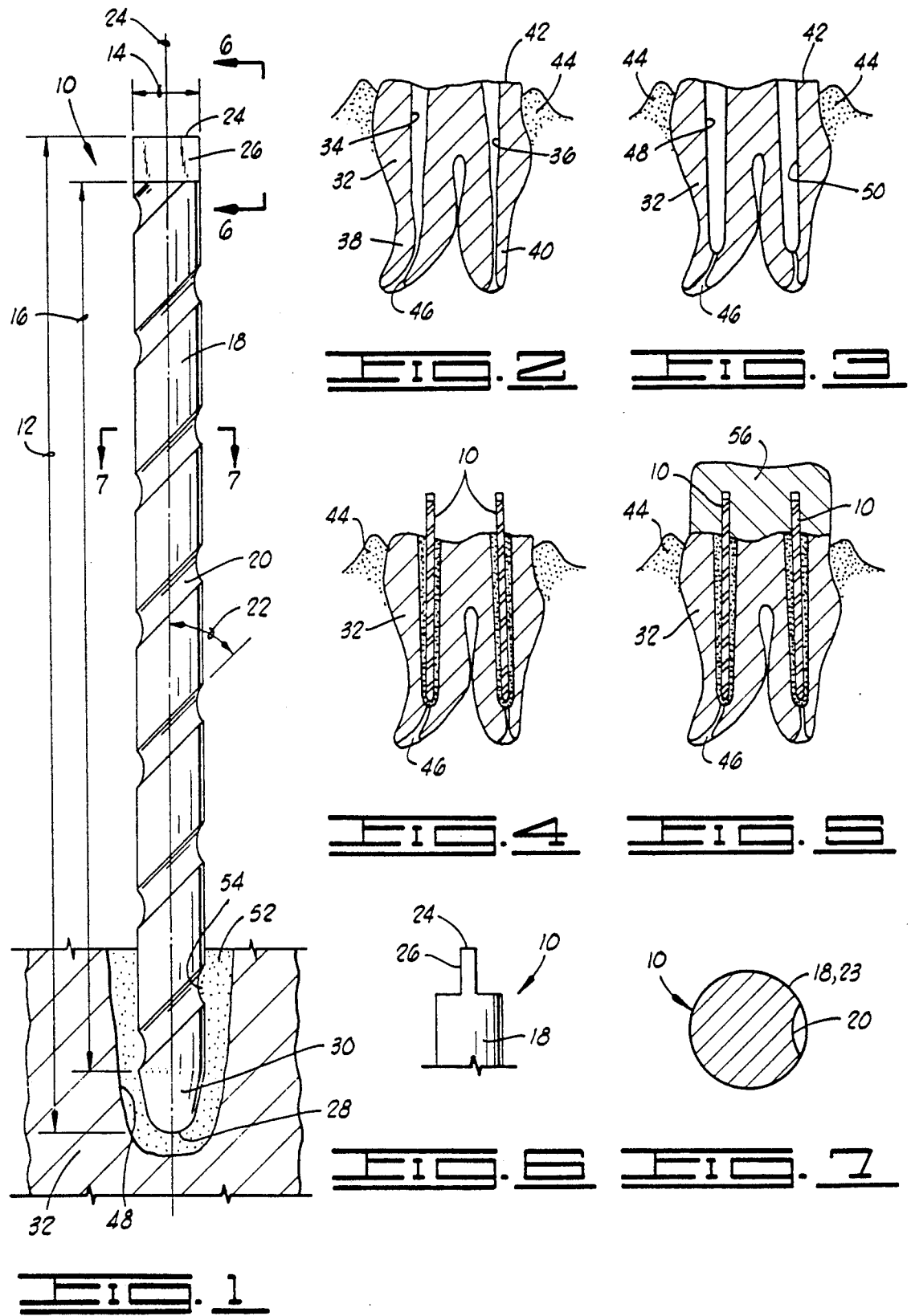

ENDODONTIC POST WITH SPIRAL GROOVE

BACKGROUND OF THE INVENTION

1. Field Of The Invention

This invention relates to an endodontic post construction for use in anchoring a tooth restoration to a portion of an injured tooth.

2. Description Of The Prior Art

When repairing severely damaged teeth, a dental post or endodontic post is often utilized to help anchor a tooth restoration such as an artificial crown to a remaining root portion of a tooth. For example, the crown may be broken from a tooth by a traumatic injury or may have substantial portions thereof removed due to removal of decayed areas, thus leaving the root or roots of the tooth along with a relatively short stub of the original crown extending above the patient's gum area.

When the damage to the tooth is such that it is necessary to remove the pulp material from the root canals, it is common to use an endodontic post to help anchor the artificial crown to the remaining original tooth structure. An endodontic post is a cylindrical pin which is cemented into the endodontically prepared root canal and extends above the surface of the remaining natural tooth to serve as an anchor for the artificial crown restoration which is attached to the remaining natural tooth.

In multi-canaled teeth such as molars, there will typically be two such posts, one placed in each of two separate canals. In single-canaled teeth, typically a single cylindrical post will be placed in the canal.

A general description of these prior art procedures utilizing endodontic posts, both in multi-canaled and single-canaled teeth is provided in "Preparing Severely Damaged Teeth", March, 1983, CDA Journal, pages 85-91 by Shillingburg, Jr., et al.

The posts utilized for such tooth restorations are typically cylindrical, often having grooves, threads or flutes formed in the post for aiding in cementing the post in place and/or venting cement from the root canal as the post is placed in the canal.

One typical prior art construction for such a post is that shown in FIG. 1 of U.S. Pat. No. 4,479,783 to Weissman. The post shown in FIG. 1 of Weissman has a spiral groove or thread 18 cut therein at a very large pitch angle to the longitudinal axis of the post. The pitch of the spiral groove is so great that it cannot effectively function as a vent. A longitudinally extending vent 24 is provided.

FIGS. 2 and 3 of U.S. Pat. No. 4,479,783 to Weissman disclose another helically fluted dental post which has a plurality of grooves placed at a very shallow (approximately 7°) pitch angle. The shallow spiral flutes of FIGS. 2 and 3 of the Weissman '783 patent function as vents, and additionally to help retain the post in place once it is cemented within a prepared root canal.

Other disclosures similar to that of FIGS. 2 and 3 of Weissman U.S. Pat. No. 4,479,783 are found in U.S. Pat. Nos. 4,729,736; 4,708,655; and 4,600,392, all also to Weissman.

U.S. Pat. No. 4,268,253 to Gross et al., discloses an endodontic post having a generally polygonal cross section which has been twisted to form a plurality of side-by-side vent grooves. The outer surface of the Gross et al. post is substantially completely covered with grooves and there is no significant non-grooved portion.

U.S. Pat. No. 4,276,027 to Lustig and U.S. Pat. No. 4,490,116 to Deutsch et al., both show endodontic posts having straight longitudinal vent grooves.

SUMMARY OF THE INVENTION

The endodontic post construction of the present invention has an elongated cylindrical outer surface with one and only one spiral groove defined in the outer surface. The groove has a pitch angle in the range of from about 35° to about 55° to the longitudinal axis of the post. This groove provides three different functions. First, it functions as a vent means for venting air and/or cement as the post is placed in an endodontically prepared root canal. Second, the groove serves as a retention means for aiding retention of the post when it is cemented in the prepared root canal. Third, the groove provides a thread means which aids in removal of the post in the event that removal is necessary.

The groove is preferably semi-circular in cross section having a radius in the range from about 5% to about 30% of a diameter of the cylindrical outer surface. An ungrooved area of the outer cylindrical surface of the post is substantially greater than a grooved area of the outer cylindrical surface.

The endodontic post of the present invention provides significant advantages over the various other post designs described above, in that a single groove functions as a vent, as a retention means, and as a thread means, while still providing a cylindrical post the majority of which is not interrupted by grooves thus providing a relatively strong post.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIG. 1 is an elevation view of the endodontic post of the present invention. A lower portion of a root canal is shown having the lower tip of the post received therein.

FIG. 2 is an elevation sectioned view of a multi-canaled tooth. The upper portion of the tooth has been broken off or removed.

FIG. 3 is a view of the tooth of FIG. 2 after the root canals have been endodontically prepared to form endodontic post spaces for receiving a post construction.

FIG. 4 illustrates the tooth of FIG. 3 after endodontic posts have been cemented in place within the prepared canals.

FIG. 5 illustrates the tooth of FIG. 4 after a tooth restoration has been mounted on the tooth and anchored by the endodontic post construction.

FIG. 6 is a partial elevation view of the upper end of the post of FIG. 1 taken along line 6—6 of FIG. 1.

FIG. 7 is a cross-sectional view of the post of FIG. 1, taken along line 7—7.

DETAILED DESCRIPTION OF THE PREFERRED EMBODIMENTS

In FIG. 1, the endodontic post of the present invention is shown and generally designated by the numeral 10. The post 10 generally has an elongated cylindrical shape, and has a length 12 and a diameter 14.

A major portion 16 of the length 12 is cylindrical in shape, having a cylindrical outer surface 18. A spiral groove 20 is defined in the cylindrical outer surface 18. There is one and only one spiral groove 20 defined in the cylindrical outer surface 18. The groove 20 is set at a pitch angle 22 to a longitudinal axis 24 of post 10. Pitch angle 22 is in a range of from about 35° to about 55°. Preferably, the pitch angle 22 is approximately 45°.

The groove 20 preferably has a smooth curvilinear cross section, and preferably is semi-circular in cross section. The semi-circular cross-section groove 20 preferably has a radius, and thus a depth within post 10, from about 5% to about 30% of the diameter 14 of the outer cylindrical surface 18 of the post 10. Preferably, the groove 20 has a depth in a range of from about 15% to about 20% of the diameter 14.

It will be appreciated by those skilled in the art that endodontic posts such as the post 10 are typically provided in several different diameters so that a suitable post can be selected to be relatively closely received within a prepared root canal of a human tooth. Typical diameters in which posts such as the post 10 are provided are 1.0 mm., 1.2 mm., 1.4 mm., and 1.6 mm. These posts typically have a length of approximately 20 mm.

The post 10 illustrated in FIG. 1 has been drawn approximately to scale to represent a 1.6 mm. diameter post, 20 mm. in length, having a groove of 0.3 mm. radius set at a pitch angle of 45°. Thus, the groove 22 spirals around the post 10 approximately six times.

As is apparent in FIG. 1, with such a construction, an ungrooved area of the outer cylindrical surface 18 is substantially greater than a grooved area of the outer cylindrical surface 18. As is apparent in FIG. 7, any cross section of the cylindrical portion 16 of post 10 comprises a circular periphery 23 interrupted at one location by groove 20. Since groove 20 is smooth in cross section, there are no significant points of stress concentration created.

This substantial ungrooved area of outer cylindrical surface 18 provides an important function in addition to the fact that it provides a strong uninterrupted cross-sectional area. It also resists rotational motion of the tooth restoration 56 relative to the post 10. This is particularly true as compared to the relative performance of a post like that of U.S. Pat. No. 4,268,253 to Gross et al. which has its entire outer surface grooved. When the tooth restoration 56 is subjected to chewing forces, those forces both push down on tooth restoration 56 and twist tooth restoration 56. When twisting forces are applied to a restoration mounted on a post like that of the Gross et al. '253 patent, the restoration tends to climb the incline of the external flutes of the post as it twists. This causes a repeated lifting force on the restoration and on the post relative to the cement which tends to break the bonds between the post and both the restoration and the cement. With the post 10 of the present invention, however, the ungrooved cylindrical surface 18 resists these twisting forces without creating a lifting force and thus provides a more secure bond between the post and both the restoration and the cement.

Post 10 has an axially outer end 24 on which is defined a wrench flat 26 which may be generally referred to as an engagement means 26 for engaging a tool, such as a wrench, for rotating the post 10 to thread the post 10 out of a prepared root canal.

An axially inner end 28 of the post 10 has a tapered and rounded tip means 30 defined thereon for minimizing stress concentrations at areas of engagement of the inner end 28 of post 10 with a tooth.

In FIG. 2, a human tooth 32 is shown. The tooth 32 illustrated is a molar tooth having two root canals 34 and 36 extending down into root portions 38 and 40 of the tooth.

An irregular upper surface 42 is shown where the tooth 32 has been broken off or cut away. Gum tissue 44 is illustrated adjacent the broken upper surface 42 of the tooth.

The root canal 34 extends downward from the upper surface 42 to an apical foramen or opening 46 in the lower end of the root 38. The root canal 36 is similarly formed.

Prior to placement of a tooth restoration or artificial crown on the tooth 32, the root canals 34 and 36 will typically be endodontically prepared in a manner well known to those skilled in the art through the use of endodontic files to enlarge the root canals 34 and 36 removing the pulp material therefrom and providing enlarged prepared root canals also referred to as endodontic post spaces 48 and 50 as illustrated in FIG. 3.

In FIG. 4, two of the posts 10 have been inserted in and cemented in place within the prepared post spaces 48 and 50.

As will be appreciated by those skilled in the art, cement may be placed within the post spaces 48 and 50 prior to insertion of the posts 10, or the posts 10 may be coated with cement prior to being inserted within the post spaces 48 and 50. Also, cement may be placed within the post spaces 48 and 50 and also coated on the posts 10 prior to insertion. In any event, the posts 10 are inserted within the post spaces 48 and 50 and cemented in place therein.

It is significant to note that the posts 10 are generally not threaded into the post spaces 48 and 50. As best illustrated in the lower portion of FIG. 1, cement 52 generally surrounds the post 10, and the post 10 is not actually tightly wedged or threaded into the post space 48. It is the cement 52 which binds the post 10 to the tooth 32, rather than a mechanical engagement of the post 10 with the tooth material 32 as is the case with many prior art threaded posts.

After the cement 52 has set, however, a spiral ridge 54 of cement is formed within the groove 20.

It is preferred that points of high stress concentration engagement of the post 10 with the post space 48 be avoided. It will be appreciated when one considers the relatively large forces which are applied to the tooth restoration 56 during the chewing of food and the like, that those forces are transmitted to a significant extent downward through the post 10 to the tooth structure 32. Sharp points of engagement between the post 10 and the tooth structure 32, particularly at the inner end 28 thereof can lead to fracturing of the tooth root.

By forming the inner end 28 of post 10 as a smooth tapered rounded tip 30, such stress concentrations are minimized.

The groove 20 of post construction 10 provides three separate important functions.

First, the groove 20 functions as a vent to vent cement and/or air from the post space 48 as the post 10 is inserted downward into the post space 48 This is particularly important when the post space 48 is filled with cement prior to insertion of the post 10.

A second function provided by the spiral groove 20 is that it aids in retention of the post 10 in place within the post space 8 by increasing the area of contact of the post 10 with the cement 52.

Finally, in the unlikely but possible event that it is necessary to remove the post 10 after the cement 52 has set, the post 10 can be readily removed by rotating it in a counterclockwise direction thus unthreading the groove 20 from the ridge 54 of cement.

It is because of this function of unthreading the post 10 to remove it from the tooth 32 that the engagement means 26 is provided on the outer end 24 of post 10. As previously noted, the post 10 is not generally threaded into place within the post space 48 but may simply be longitudinally inserted into the post space 48. It is, however, threaded out of the post space 48 after the cement 52 has set.

A curvilinear cross-section shape and particularly the semicircular cross-section shape previously described for groove 20 is preferred as compared to a square or triangular cross-section groove as it eliminates points of stress concentration within the post 10. This, combined with the fact that only a single groove interrupts any cross section of the post 10, reduces the possibility of breakage of the post 10 when subjected to chewing forces.

Thus it is seen that the apparatus and methods of the present invention readily achieve the ends and advantages mentioned as well as those inherent therein While certain preferred embodiments of the invention have been illustrated and disclosed for purposes of the present disclosure, numerous changes in the arrangement and construction of parts and steps may be made by those skilled in the art which changes are encompassed within the scope and spirit of the present invention as defined by the appended claims.

What is claimed is:

1. An endodontic post constructed to be inserted into a prepared post space in a tooth root and cemented in place therein for anchoring a tooth restoration, comprising:
   an elongated post having a generally cylindrical outer surface extending over substantially an entire length of said post;
   one and only one spiral groove defined in said outer surface of said post, said groove having a pitch angle in a range of from about 35° to about 55° so that said groove provides:
      a vent means for venting air and/or cement as said post is placed in said prepared post space;
      a retention means for aiding retention of said post when said post is cemented in said prepared post space; and
      a thread means for threading said post out of said prepared post space in the event of removal of said post; and
   wherein an ungrooved area of said cylindrical outer surface of said post is substantially greater than a grooved area of said cylindrical outer surface.

2. The endodontic post of claim 1, wherein said pitch angle is approximately 45°.

3. The endodontic post of claim 1, wherein said groove has a smooth curvilinear cross section.

4. The endodontic post of claim 3, wherein said groove is semi-circular in cross section 5. The endodontic post of claim 4, wherein said semi-circular cross section of said groove has a radius in a range of from about 5% to about 30% of a diameter of said cylindrical outer surface of said post.

6. The endodontic post of claim 1, wherein said groove has a depth in a range of from about 5% to about 30% of a diameter of said cylindrical outer surface of said post.

7. The endodontic post of claim 1, further comprising:
   engagement means, defined on an axially outer end of said post for engaging a tool for rotating said post to thread said post out of said prepared post space in the event of removal of said post.

8. The endodontic post of claim 1, further comprising:
   a tapered and rounded tip means defined on an axially inner end of said post, for minimizing stress concentrations at areas of engagement of said inner end with said tooth.

9. A method of anchoring a tooth restoration, said method comprising the steps of:
   providing an endodontic post having a generally cylindrical outer surface and one and only one spiral groove defined in said outer surface, said groove having a helix angle in a range of from about 35° to about 55°, an ungrooved area of said outer cylindrical surface being substantially greater than a grooved area thereof;
   inserting said post into a prepared post space of a tooth and cementing said post therein;
   venting air and/or cement through said groove as said post is inserted into said prepared post space;
   retaining said post in said prepared post space at least partly by means of cement being received in and set up in said groove; and
   mounting said tooth restoration about said post.

10. The method of claim 9, further comprising a step of:
   after said post is cemented in said prepared root canal, removing said post from said prepared post space by rotating said post and unthreading said groove from a ridge of cement formed therein.

* * * * *